United States Patent [19]

Larkin et al.

[11] 4,441,538

[45] Apr. 10, 1984

[54] FLEXIBLE CONTAINER WITH INTEGRAL PORTS AND DIAPHRAGM

[75] Inventors: Mark E. Larkin, Lindenhurst; Leonard J. Meyer, Antioch, both of Ill.

[73] Assignee: Abbott Laboratories, North Chicago, Ill.

[21] Appl. No.: 298,987

[22] Filed: Sep. 3, 1981

Related U.S. Application Data

[62] Division of Ser. No. 106,954, Dec. 26, 1979, Pat. No. 4,313,904.

[51] Int. Cl.[3] .................................. A61M 5/14

[52] U.S. Cl. .................................. 604/415; 215/247

[58] Field of Search .................. 150/8, 0.5; 215/247, 215/249, 248

[56] References Cited

U.S. PATENT DOCUMENTS

| | | | |
|---|---|---|---|
| 3,092,278 | 6/1963 | Jarnhall | 215/247 |
| 3,554,256 | 1/1971 | Anderson | 150/8 |
| 3,642,047 | 2/1972 | Waage | 150/8 |
| 3,810,503 | 5/1974 | Lewis et al. | 150/8 |
| 3,915,212 | 10/1975 | Bujan et al. | 150/8 |
| 3,977,553 | 8/1976 | Cornett et al. | 215/249 X |
| 4,096,897 | 6/1978 | Cammarata | 150/0.5 |
| 4,178,976 | 12/1979 | Weiler et al. | 150/0.5 |
| 4,226,334 | 10/1980 | Weiler et al. | 150/0.5 X |

*Primary Examiner*—Donald F. Norton

*Attorney, Agent, or Firm*—Robert S. Beiser; Robert L. Niblack

[57] ABSTRACT

A container for liquids, preferably sterile liquids comprises a hollow body constructed of plastic material having a plurality of tubular ports integrally formed and extending therefrom. Each port has a quantity of plastic material integrally formed as a diaphragm within the port so as to seal the container. In a preferred embodiment, at least one of the ports has a resealable septum sealed within it. The diaphragm is positioned between the septum and the liquid within the container so as to prevent deterioration of the resealable septum caused by exposure to the liquid. Both the resealable septum and the diaphragm are constructed of a material which is penetrable by a hypodermic needle for use in administering sterile solutions.

8 Claims, 4 Drawing Figures

FLEXIBLE CONTAINER WITH INTEGRAL PORTS AND DIAPHRAGM

This is a division of application Ser. No. 106,954 filed Dec. 26, 1979, now U.S. Pat. No. 4,313,904.

BACKGROUND OF THE INVENTION

The present invention relates generally to containers for liquids, and in particular, to containers for liquid medicinal products, such as for example, intravenous solutions such as electrolytic or other solutions, plasma substitute solutions, anticoagulant solutions, blood or plasma and derivatives.

Plastic molded containers have found increasing acceptance in recent years and are used extensively throughout the packaging field due to the fact that they are relatively inexpensive, lighter in weight, durable and resist degradation from the liquids they contain. In the medical field, a particularly wide acceptance has been found for flexible containers used for dispensing liquids such as intravenous solutions. A continuing problem exists however in reducing the manufacturing costs of said containers. An additional problem has been the manufacture of such containers having a number of ports attached thereto for adding additional liquid to the container such as a medicament, or for filling the container itself prior to sterilization.

Accordingly, it is an advantage of the present invention to provide a container for liquids which is low cost and easy to manufacture. It is an additional advantage of the invention to provide a container for sterile liquids which has a number of tubular ports integrally formed and extending therefrom during the same forming process as the container itself.

An additional problem in this regard has been the injection of liquids through one of the tubular ports. At the present time resealable septums are commonly used in such ports. However the liquids within such containers usually have a deleterious effect upon such resealable septums, which are usually constructed of a rubber material. Accordingly it is an additional advantage of the invention to provide a container for liquids which has a diaphragm integrally formed in each tubular port so as to separate the liquid contained within the container from the resealable septum within the tubular port, thereby preventing deterioration of the septum.

SUMMARY OF THE INVENTION

The present invention is a container for liquids comprising a hollow body formed of plastic material. A number of tubular ports, preferably two, are integrally formed in and extend from the hollow body. Each port has a diaphragm integrally formed within it from the same plastic material.

In a preferred embodiment each tubular port also contains a resealable septum sealed within the port. The diaphragm is positioned between the resealable septum and the liquid within the container so as to prevent deterioration of the resealable septum from exposure to the liquid. The resealable septum and the diaphragm are both constructed of a material which allows penetration by a hypodermic needle. The resealable septum, preferably constructed of a rubber compound, is designed to reseal itself upon removal of the hypodermic needle.

In a preferred embodiment the resealable septum is positioned within the tubular port during formation of the container, so as to provide improved seal characteristics between the septum and the tubular port. The container is blow-molded in the shape of a flexible bag, particularly adapted for dispensing sterile solutions. In such an embodiment, the bag is formed as a hollow body which is substantially tubular in shape, tapering at one end to a hanger portion and having at least one tubular port at a second end. The bag is adapted for hanging vertically and dispensing liquid from the container through the tubular port. Along these same lines the shape of the container and the material selected effectively cause the bag to collapse uniformly from top to bottom upon dispersal of the liquid from the container. Thus, the invention is particularly well adapted for use in sterilizable and sterility maintaining packaging. An additional means of ensuring such sterility is the use of an overcap over each tubular port so as to prevent contamination of the port after sterilization and before penetration by a hypodermic needle.

The invention also comprises a method of manufacturing a flexible plastic container for sterile solutions having at least one tubular port integrally formed therein. Conventional blow-molding of a plastic material for sterile solutions comprises the steps of extruding a parison of heated plastic material into a mold having portions shaped as a hollow cavity and tubular ports. The parison is then blown into the shape of the mold. The present invention represents an improvement over conventional technology in the additional steps of inserting a pair of diaphragm pins into the lower portion of the parison for each tubular port desired. In a preferred embodiment the diaphragm pins are coaxially aligned, one inside and one outside of the parison. A portion of the heated plastic material is squeezed into the portion of the mold shaped as each tubular port. Part of the heated plastic is retained across the opening of that portion of the mold shaped as a tubular port, thus forming a diaphragm isolating the port from the remainder of the container. The material is then cooled sufficiently to retain the shape of the mold, the diaphragm, and each of said ports. The diaphragm pins are then retracted and the container is removed from the mold.

An additional feature of the invention, in a preferred embodiment, is the formation of the previously mentioned ports with resealable septums integrally formed therein. This is accomplished by affixing a septum to each diaphragm pin positioned outside the parison before insertion into the parison. A tubular port and diaphragm are then formed about each resealable septum. The septum is then released from the diaphragm pin after cooling of the container.

One means of affixing the septum to the diaphragm pin is by using a point on the end of the pin which is adapted for puncturing the septum sufficiently to affix and retain it during the manufacturing process. This allows simplified, low cost manufacture. An additional feature of the invention is that by formation of the diaphragm in the tubular ports the container may be both blown, filled and sealed within the mold in a sterile condition, (the sterile condition of the container during formation is caused by the heated condition of the plastic).

DETAILED DESCRIPTION OF A PREFERRED EMBODIMENT

Figure 1:
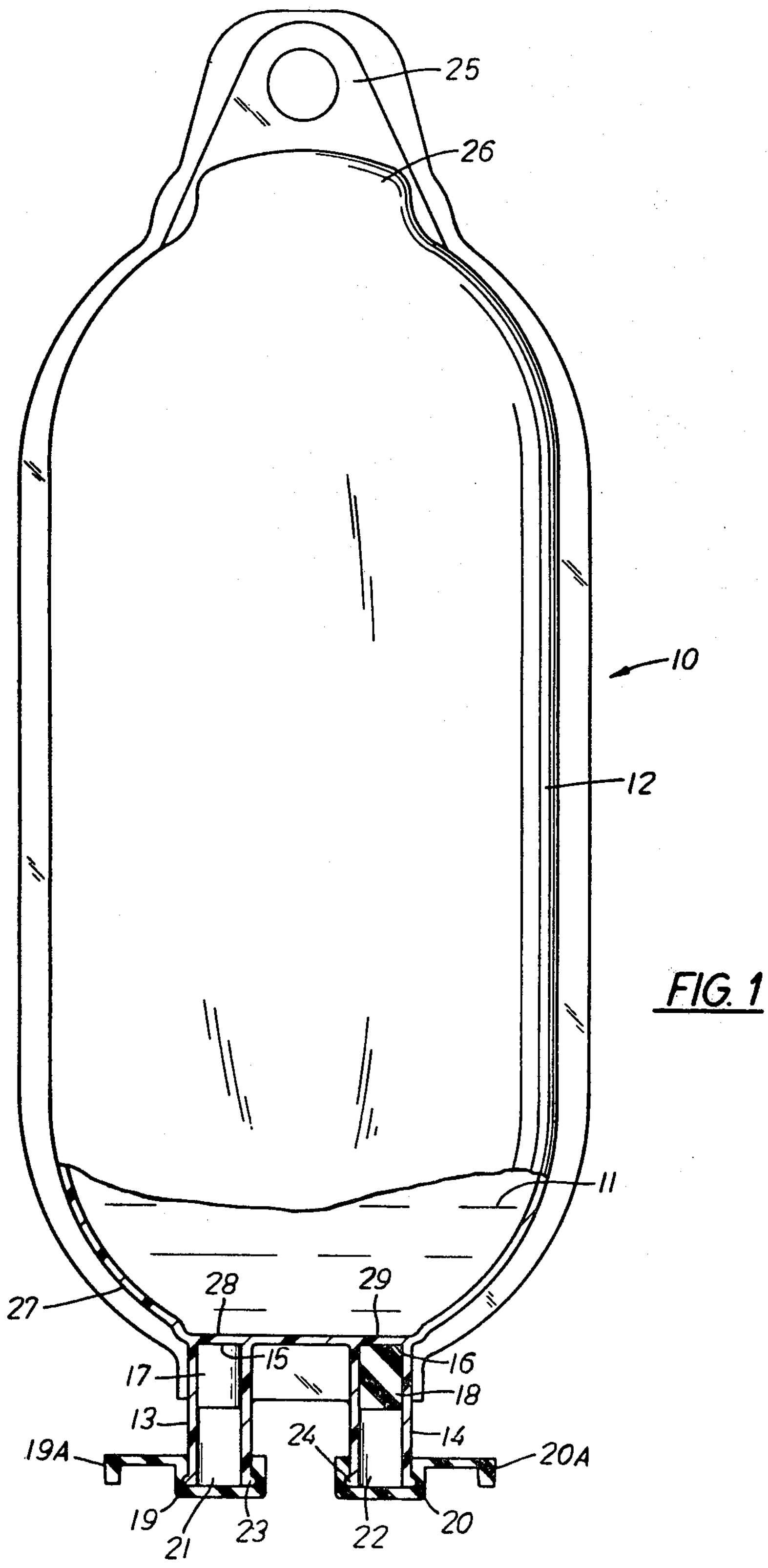
FIG. 1 of the drawings is a front view, partially cutaway, of a container for liquids formed as a hollow body having a pair of tubular ports integrally formed and extending therefrom.

While this invention is susceptible of embodiment in many different forms, there is shown in the drawings and will herein be described in detail, several specific embodiments, with the understanding that the embodiments illustrated are an exemplification of the principles of the invention, and are not intended to limit the invention to the embodiments illustrated.

Container 10 for liquid 11 comprises a hollow body 12 formed of plastic material such as polyethylene, polypropylene, polyvinylchloride or other commonly known plastics. Hollow body 12 has tubular ports 13 and 14 integrally formed and extending therefrom. Formed within tubular ports 13 and 14 are diaphragms 15 and 16 which seal ports 13 and 14 from hollow body 12 and correspondingly seal liquid 11 from the atmosphere.

In a preferred embodiment tubular ports 13 and 14 contain resealable septums 17 and 18 which are fixably attached and sealed therein. Septums 17 and 18 are formed preferably of butyl rubber, silicone rubber, or other commonly known elastomers. Diaphragms 15 and 16 are positioned between septums 17 and 18 and liquid 11 so as to prevent deterioration of septums 17 and 18 from exposure to liquid 11. Septums 17 and 18 as well as diaphragms 15 and 16 are adapted for penetration by a hypodermic needle (not shown). In addition septums 17 and 18 are adapted to reseal themselves upon withdrawal of the hypodermic needle. In a preferred embodiment resealable septums 17 and 18 are positioned within tubular ports 13 and 14 during the formation of container 10 so as to provide improved sealing characteristics between septums 17 and 18 and tubular ports 13 and 14. Thus, in a preferred embodiment container 10 is both sterilizable and sterility maintaining in order to contain sterile solutions. Along these same lines, in a preferred embodiment container 10 includes overcaps 19 and 20 affixed to tubular ports 13 and 14. Overcap 19 is designed to cover orifice 21 of tubular port 13. Similarly, overcap 20 is designed to cover orifice 22 of tubular port 14. One means for retaining overcaps 19 and 20 on tubular ports 13 and 14 is through the use of flanges 23 and 24 formed respectively on tubular ports 13 and 14. Overcaps 19 and 20 are formed of flexible thermoplastic materials so as to snap over flanges 23 and 24 and thereby be retained on tubular ports 13 and 14. Thus attached overcaps 19 and 20 are sterility maintaining, but may be removed before insertion of a hypodermic needle by means of tabs 19A and 20A.

In a preferred embodiment container 10 and hollow body 12 are formed in a substantially tubular shape tapering to a hanger 25 at end 26. Tubular ports 13 and 14 are formed at end 27. As a result when container 10 is hung with hanger 25 in the uppermost position ports 13 and 14 below liquid 11 may be dispensed by gravity feed. In addition, hollow body 12 is constructed of material sufficiently elastic and is shaped so as to uniformly collapse from hanger portion 25 downward. In order to accomplish this, in a preferred embodiment, container 10 comprises a blow-molded bag constructed of such materials as plasticized polyvinyl chloride polymers.

The invention also includes a method of manufacturing flexible container 10.

Figure 2:
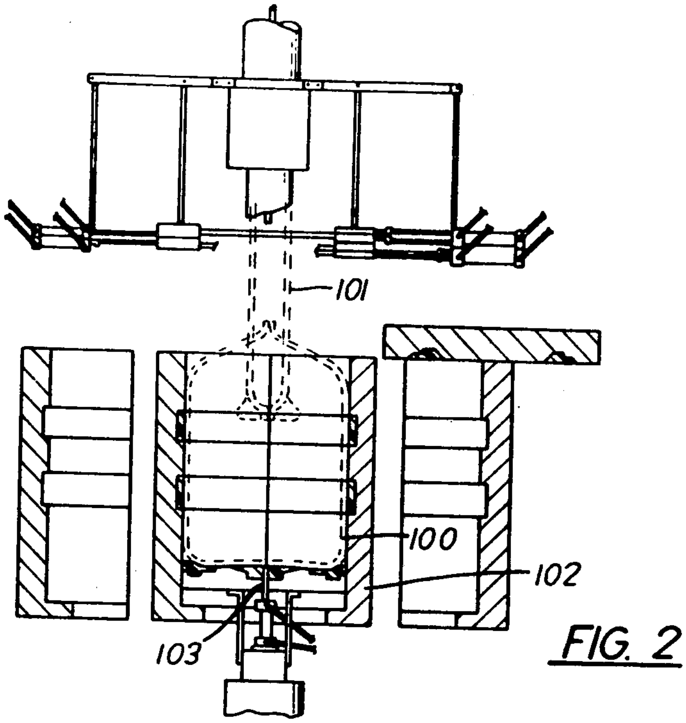
FIG. 2 of the drawings is a front cut-away schematic view showing a prior art method of manufacturing a blow-molded container.

As shon in FIG. 2 of the drawings one conventional method of manufacturing a blow-molded plastic container 100 comprises the steps of extruding a parison 101 of heated plastic material into a mold 102, blowing the parison 101 into the shape of the mold 102 utilizing a blow pipe 103, cooling container 100 and removing it from mold 102. Also known in the art is the formation of tubular ports (not shown) extending from container 100. Additionally taught in the prior art, as seen in U.S. Pat. No. 3,919,374 is the formation of a tubular port in a blow-molding process in which a rubber plug is introduced into the tubular port during the blow-molding process and the tubular ports are formed about the rubber plug.

Figure 3:
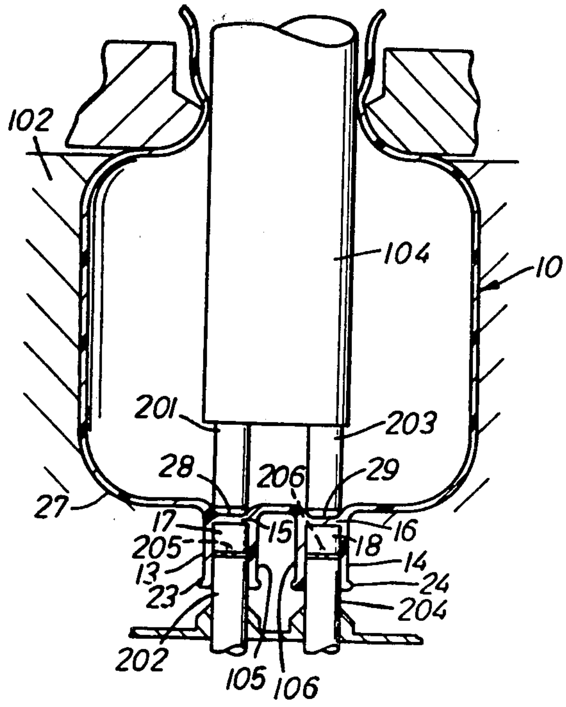
FIG. 3 of the drawings is a front cut-away view of a method of manufacture of the container of FIG. 1 showing in particular adjustable diaphragm pins for the formation of a diaphragm within the container.

The present invention represents an improvement over the prior art in that, as seen in FIG. 3 of the drawings, after container 10 is extruded as a parison of heated plastic material into a mold 102, diaphragm pins 201, 202, 203 and 204 are used for forming diaphragms 15 and 16. Pin 201 within container 10 is coaxially aligned to pin 202 outside container 10. Similarly pin 203 is coaxially aligned to pin 204. Pins 201 through 204 are used to squeeze end portion 27 of the plastic material at the bottom of container 10 into sections 105 and 106 of mold 102 which are shaped as tubular ports. A portion of the thermoplastic material is retained across openings 28 and 29 which lead to tubular ports 13 and 14. This retained plastic material forms diaphragms 15 and 16. Container 10 is then cooled so as to retain the shape of forming mold 102. Diaphragm pins 201 through 204 are then removed from mold 102 and container 10 is similarly removed from the mold.

Figure 4:
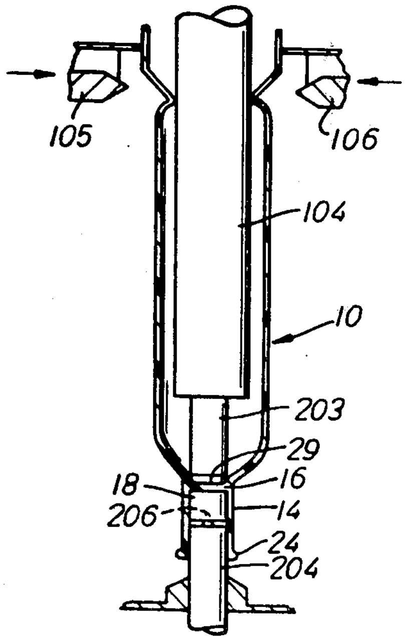
FIG. 4 of the drawings is a side cut-away view of the method of manufacture as shown in FIG. 3.

In a preferred embodiment, as seen in FIGS. 3 and 4, resealable septums 17 and 18 are affixed to diaphragm pins 202 and 204, and tubular ports 13 and 14 and diaphragms 15 and 16 are then formed about resealable septums 17 and 18. Septums 17 and 18 are then released from diaphragm pins 202 and 204 after cooling of container 10 and pins 202 and 204 are removed from tubular ports 13 and 14. Container 10 is then removed from the mold. As seen in FIG. 3 diaphragm pins 202 and 204 contain points 205 and 206 which are used to affix septums 17 and 18 and retain them on a diaphragm pins 202 and 204. Such fixation and insertion allows high speed manufacture of blow-molded containers such as container 10.

As further shown in FIG. 4 of the drawings container 10 may be formed using blow pin 104 which is adapted either for blowing container 10 into shape within the mold or may additionally be adapted for filling container 10 with liquid 11 while in the mold. Blow pin 104 is then removed from container 10 and the top portion of container 10 is sealed using sealing knives 105 and 106 which seal the top portion 26 of container 10 and in a preferred embodiment also form hanger 25 proximate to top portion 26.

The foregoing description and drawings merely explain and illustrate the invention, and the invention is not limited thereto, except in so far as the appended claims are so limited as those skilled in the art who have the disclosure before them will be able to make modifications and variations therein without departing from the scope of the invention.

We claim:

1. A container for liquids comprising a hollow body formed of a plastic material; said hollow body having a plurality of tubular ports integrally formed from said plastic material of said hollow body and extending therefrom; each of said ports having a quantity of said plastic material integrally formed as a diaphragm within said port from said plastic material of said tubular port so as to seal said port.

2. The invention according to claim 1 in which at least one of said tubular ports contains a resealable septum member fixedly attached and sealed therein, said diaphragm being positioned between said resealable septum and liquid within said container so as to prevent deterioration of said resealable septum from exposure to said liquid; said resealable septum and said diaphragm being adapted for penetration by a hypodermic needle.

3. The invention according to claim 2 in which said tubular port is formed about said resealable septum so as to provide improved sealability between said septum and said tubular port.

4. The invention according to claim 1 or 2 further including a plurality of overcap members affixed to and covering said tubular ports so as to prevent contamination of said ports.

5. The invention according to claim 4 further including tab means attached to said overcap members for facilitating removal of said overcap members from said tubular ports.

6. The invention according to claim 1 in which said hollow body is substantially tubular in shape, tapering to a hanger portion at one end and having at least one of said tubular ports at a second end, said hollow body being adapted to substantially uniformly collapse from said hanger portion downward upon dispersal of said liquid from said container.

7. The invention according to claim 1 in which said container comprises a blow molded bag.

8. The invention according to claim 1 in which said container is sterilizable and sterility maintaining.

* * * * *